US00PP25050P3

(12) United States Plant Patent
Suphachadiwong

(10) Patent No.: US PP25,050 P3
(45) Date of Patent: Nov. 11, 2014

(54) ***PHALAENOPSIS* PLANT NAMED 'SUPHAL1306'**

(50) Latin Name: ***Phalaenopsis* hybrid**
Varietal Denomination: SUPHAL1306

(71) Applicant: Thumrong Suphachadiwong, Chonburi (TH)

(72) Inventor: Thumrong Suphachadiwong, Chonburi (TH)

(73) Assignee: Suphachatawong Innovation (TH)

( * ) Notice: Subject to any disclaimer, the term of this patent is extended or adjusted under 35 U.S.C. 154(b) by 35 days.

(21) Appl. No.: 13/815,797

(22) Filed: Mar. 15, 2013

(65) Prior Publication Data

US 2014/0283260 P1 Sep. 18, 2014

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Cassandra Bright

(57) ABSTRACT

A new and distinct *Phalaenopsis* cultivar named 'SUPHAL1306' is disclosed, characterized by short plant height, purple and white netted petals and sepals, as well as strongly netted dorsal sepals and a lip that is dark purple with yellow base and dark purple lateral stripe. The new variety is a *Phalaenopsis*, typically produced as an indoor ornamental plant.

2 Drawing Sheets

Figure 1:
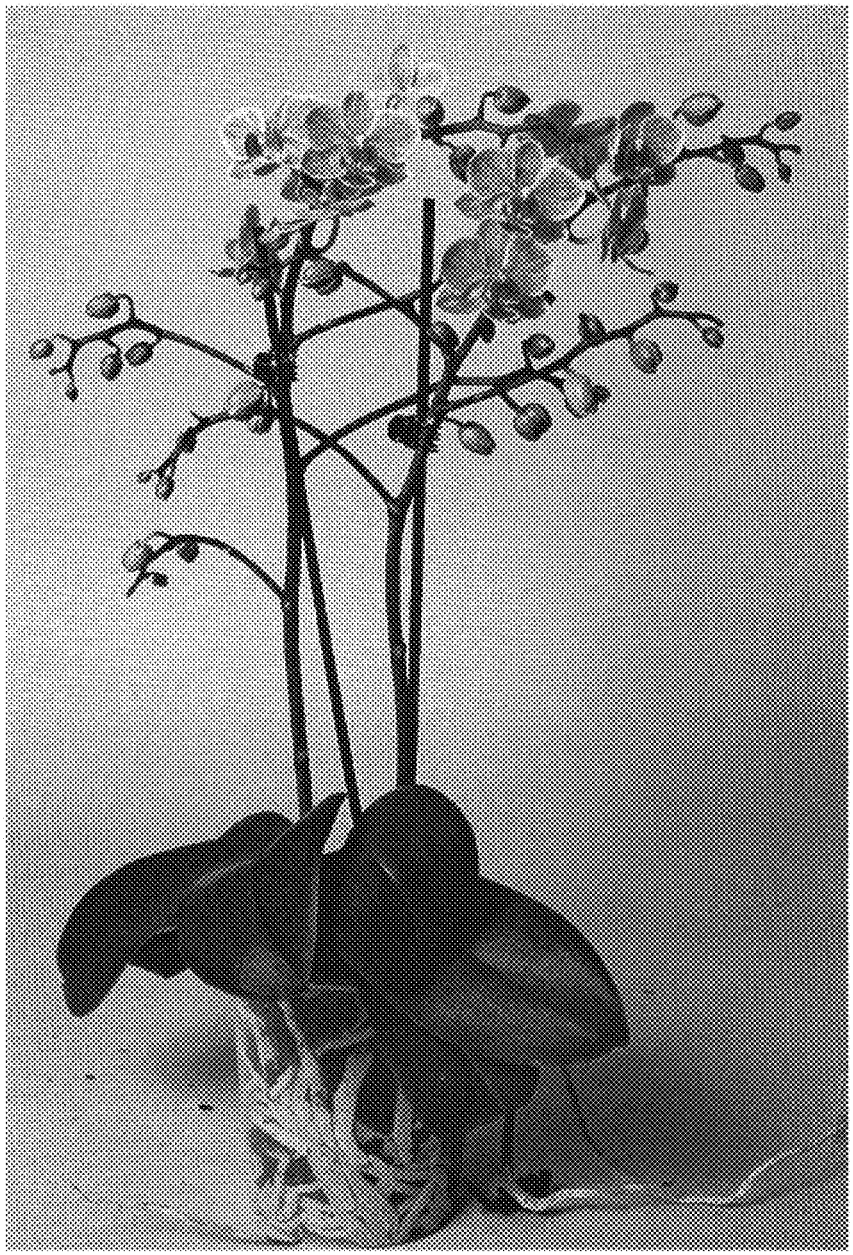

Latin name of the genus and species: *Phalaenopsis* hybrid.
Variety denomination: 'SUPHAL1306'.

BACKGROUND OF THE INVENTION

This application relates to a new cultivar of *Phalaenopsis* hybrid. The new variety is the product of a planned breeding program. The new variety originated as a seedling from the crossing of the unpatented, proprietary seed parent *Phalaenopsis* 'SHH1S7' with the unpatented, proprietary pollen parent referred to as *Phalaenopsis* 'PFM3CSS7'. The crossing was made by the inventor in his research greenhouse in Chonburi, Thailand in September of 2005.

The new variety was first selected by the inventor, Thumrong Suphachadiwong, a citizen of Thailand, in October of 2008 in a research greenhouse belonging to the inventor in Chonburi, Thailand. After, identifying the new variety as a potentially interesting selection, the inventor continued confidential testing and propagation of 'SUPHAL1306', assessing stability of the unique characteristics of this variety.

Asexual reproduction of the new cultivar 'SUPHAL1306' was first performed at a commercial laboratory belonging to the inventor in Chonburi, Thailand by tissue culture in October of 2008. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SUPHAL1306' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUPHAL1306'. These characteristics in combination distinguish 'SUPHAL1306' as a new and distinct *Phalaenopsis* cultivar:

1. Short plant height.
2. Petals and sepals are purple netted with white margins.
3. Dorsal sepals are strongly netted.
4. Lip is dark purple with yellow base and a dark purple lateral stripe.

PARENT COMPARISON

Plants of the new cultivar 'SUPHAL1306' are similar to the seed parent, *Phalaenopsis* 'SHH1S7' in most horticultural characteristics. The new variety, however, produces a more compact plant than the seed parent. Additionally, the new variety produces smaller flowers than the seed parent.

Plants of the new cultivar 'SUPHAL1306' are similar to the pollen parent, *Phalaenopsis* 'PFM3CSS7' in most horticultural characteristics. Plants of the new variety however produce larger flowers than the pollen parent.

COMMERCIAL COMPARISON

'SUPHAL1306' is similar to the unpatented commercial variety *Phalaenopsis* 'Olivia' in most horticultural characteristics. However the new variety, 'SUPHAL1306' differs from 'Olivia' in the following characteristics:

1. Sepal and petal shape.
2. Petals are further apart.
3. Purple apical lobe with white margin and yellow base, whereas 'Olivia' has a reddish purple apical lobe.
4. Smaller flower size.

5. Netting has less contrast.
6. Leaves are darker green.

BRIEF DESCRIPTION OF THE PHOTOGRAPH

The accompanying photographs in FIG. 1 illustrates in full color a typical plant of 'SUPHAL1306' grown in a commercial greenhouse in Zuidbroek, the Netherlands. This plant is approximately 18 months old after deflasking, shown planted in an 11 cm container.

Figure 2:
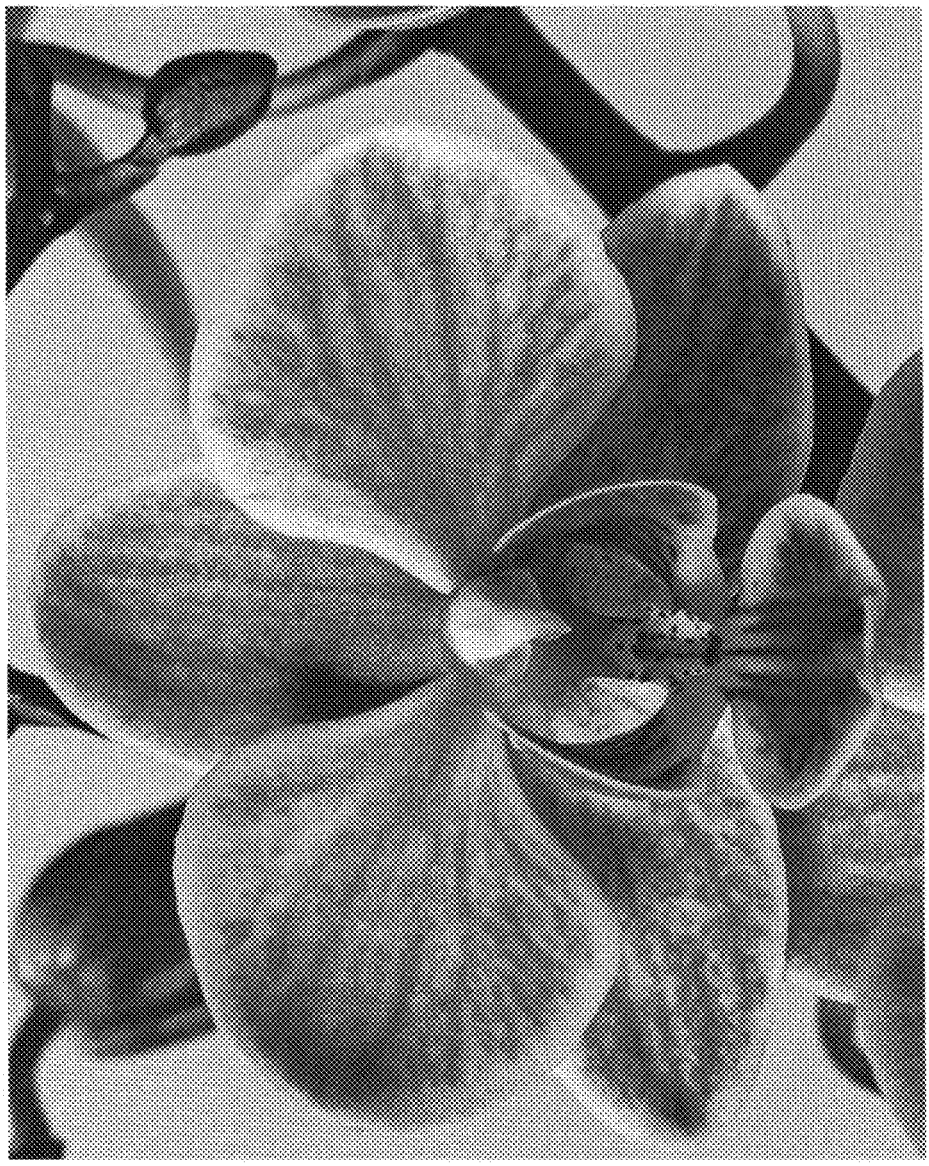

FIG. 2 illustrates a close up of the individual flower. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SUPHAL1306' plants grown in a commercial greenhouse in Zuidbroek, the Netherlands. This plant is approximately 18 months old after deflasking, shown planted in an 11 cm container. Temperatures ranged between 18° C. and 28° C. day and night. No photoperiodic or chemical treatments were given to the plants. During bright Summer conditions, shade was given. During dark Winter months, supplemental light was given at unspecified amounts. Measurements and numerical values represent averages of typical plant types.

Botanical classification: *Phalaenopsis* hybrid 'SUPHAL1306'.

PROPAGATION

Type of propagation typically used: Tissue culture.
Time to initiate roots: About 21 days at approximately 28° C.
Time to produce a rooted cutting/liner: About 26 weeks at approximately 18° C. to 28° C.
Root description: Thick (typical for *Phalaenopsis*) and rounded, average diameter: 5 mm, colored greyed-green; near RHS 194B.

PLANT

Growth habit: Monopodial.
Height from top of soil line to top of foliage: Average 7.4 cm.
Height from top of soil line to top of flowers: Average 35.3 cm.
Plant spread: At widest, average: 33.5 cm; at narrowest: 19.8 cm.
Normal pot size: 11 cm.
Growth rate: Moderate.
Number of leaves per plant: Average 9.

FOLIAGE

Leaf:
- *Arrangement*.—Distichous.
- *Average length*.—Approximately 14.5 cm (including sheath).
- *Average width*.—Approximately 7.2 cm.
- *Shape of blade*.—Ovate to elliptic.
- *Aspect*.—Horizontal to slightly downward.
- *Apex*.—Unequal acute, curled downward.
- *Base*.—Cuneate. Sheath length: Average 1.4 cm. Sheath width: Average 1.2 cm. Sheath color: Green; near RHS 143C.
- *Margin*.—Entire.
- *Texture of top surface*.—Smooth, slightly furrowed.
- *Texture of bottom surface*.—Smooth.
- *Appearance of top surface*.—Moderately glossy.
- *Appearance of bottom surface*.—Moderately glossy.
- *Color*.—Young foliage upper side: Green; near RHS N137A. Young foliage under side: Green; near RHS 137C moderately tinged greyed-purple, near RHS N186C. Mature foliage upper side: Green; near RHS N137A. Mature foliage under side: Yellow-green; near RHS 146B.
- *Venation*.—Type: Camptodromous. Venation coloration: Upper side green; near RHS N137D, under side yellow-green; near RHS 146B, main vein on under side yellow-green; near RHS 144A.

Petiole: No petiole present.

FLOWERING CHARACTERISTICS

Flower bud:
- *Rate of opening*.—Approximately five days after stage described.
- *Length*.—Approximately 1.4 cm.
- *Diameter*.—Approximately 1.0 cm wide and 1.3 cm high.
- *Shape*.—Broad ovate.
- *Color*.—Green; near RHS 145B, moderately to heavily tinged purple; near RHS 77B.

Peduncle:
- *Length*.—Approximately 39.5 cm.
- *Width*.—Approximately 0.6 cm.
- *Aspect*.—Approximately 70° angle to rosette.
- *Strength*.—Strong.
- *Texture*.—Smooth.
- *Appearance*.—Slightly glossy.
- *Color*.—Green to greyed-green; in between RHS 137C and 191A, moderately to heavily dotted green; near RHS 138D.

Inflorescence:
- *Flowers per stem*.—Average 33.
- *Inflorescence arrangement*.—Compound panicle.
- *Inflorescence height*.—Approximately 20.5 cm (measured from lowest branching of panicle to top of inflorescence).
- *Inflorescence width*.—Approximately 22.7 cm.

Individual flowers:
- *Flower type*.—Single zygomorphic flower.
- *Shape*.—Rounded deltate.
- *Length (height)*.—Approximately 4.8 cm.
- *Width*.—Approximately 4.8 cm.
- *Depth*.—Approximately 1.8 cm.
- *Fragrance*.—No fragrance.
- *Persistent*.—Non-persistent.
- *Quantity of petals*.—2 true petals.

Petals:
- *Arrangement*.—One petal on each side of the column.
- *Length*.—Approximately 2.3 cm.
- *Width*.—Approximately 2.2 cm.
- *Shape*.—Broad ovate to near deltoid.
- *Apex*.—Obtuse.
- *Base*.—Cuneate.
- *Margin*.—Entire.

*Texture*.—Upper (forward) surface: Smooth, velvety.
*Texture*.—Lower (back) surface: Smooth, velvety.
*Appearance*.—Matte on both surfaces.
*Color*.—When opening, forward surface: Purple; near RHS 77D, margins white; near RHS NN155D. When opening, back surface: Purple; near RHS 77D, margins white; near RHS NN155D. Fully Opened, forward surface: Purple; near RHS 77D, margins white; near RHS NN155D. Fully Opened, back surface: Purple; near RHS 77D, margins white; near RHS NN155D. Fading, forward surface: Not fading, only becoming non-velvety. Fading, back surface: Not fading, only becoming non-velvety.
*Color venation*.—Fully Opened, forward surface: Red-purple; near RHS 72B. Fully Opened, back surface: Purple; near RHS 77B.

Labellum:
*Shape*.—Three-parted.
*Length*.—Approximately 2.3 cm.
*Width*.—Approximately 1.5 cm.
*Texture*.—Smooth, slightly velvety.
*Appearance*.—Matte.
*Tip*.—Straight.
*Base*.—Cuneate.
*Color*.—When opening, forward surface: Central lobe red-purple to purple; in between RHS 71A and N79C. Margin white at the top; near RHS NN155D and yellow at the base; near RHS 9C. Lateral lobes red-purple to purple; in between RHS 71A and N79C, lower margin yellow; near RHS 10B, callosities yellow; near RHS 11D, dotted purple; near RHS N77A. When opening, back surface: Central lobe purple-violet; near RHS N80C, margin white at the top; near RHS NN155CD and yellow at the base; near RHS 11A, lateral lobes purple; near RHS 77B, darker towards the margins; near RHS 77A, lower margin yellow; near RHS 8C to 8D. Fully Opened, forward surface: Central lobe purple; near N79C, margin white at the top; near RHS NN155D and yellow at the base; near RHS 9C, lateral lobes purple; near N79C, lower margin yellow; near RHS 10B, callosities yellow; near RHS 11D, dotted purple; near RHS N77A. Fully Opened, back surface: Central lobe purple-violet; near RHS N81C, margin white at the top; near RHS NN155C and yellow at the base; near RHS 11A, lateral lobes purple; near RHS 77B, darker towards the margins; near RHS 77A, lower margin yellow; near RHS 8C. Fading, forward surface: Not fading, only becoming non-velvety. Fading, back surface: Not fading, only becoming non-velvety.
*Color venation*.—Fully Opened, forward surface: No venation visible Fully Opened, back surface: An average of five straight main veins is colored red-purple; near RHS 59A. Margin: Entire.

Sepals:
*Quantity*.—3.
*Length*.—Approximately 2.3 cm.
*Width*.—Approximately 1.6 cm.
*Shape*.—Ovate, dorsal sepal ovate to elliptic.
*Apex*.—Broad bluntly acute to obtuse.
*Base*.—Broad cuneate.
*Margin*.—Entire.
*Texture*.—Smooth, velvety.
*Appearance*.—Matte.
*Color*.—Fully Opened, forward surface: Purple; near RHS 76A, heavily marbled darker; near RHS N78A, except for a small part at the base of the lateral sepals, margins white; near RHS NN155C.
*Fully opened, back surface*.—Purple; near RHS 76B, heavily marbled darker; near RHS 77B to 77C, main vein coloured red-purple at the top; near RHS 72B, margins white; near RHS NN155C.

Pedicels:
*Length*.—Approximately 2.5 cm.
*Diameter*.—Approximately 0.2 cm.
*Angle*.—Approximately 85° to peduncle.
*Strength*.—Moderately strong.
*Texture*.—Smooth.
*Appearance*.—Moderately glossy.
*Color*.—Greyed-purple; near RHS 186C, purple at distal end; near RHS 75B, yellow-green at the base; near RHS 152C.

REPRODUCTIVE ORGANS

Stamens, style and stigma fused into column?: Yes.
Column length: Approximately 0.9 cm.
Column diameter: approximately 0.5 cm.
Column color: Purple-violet; near RHS N80A.
Ovary:
*Position*.—Inferior.
*Diameter*.—Approximately 0.3 cm.
*Color*.—Red-purple; near RHS N74C.
Pollen color: Yellow-orange; near RHS 21A.

OTHER CHARACTERISTICS

Disease resistance: Neither resistance nor susceptibility to the normal diseases found in *Phalaenopsis* has been observed.
Drought tolerance and cold tolerance: Normal for species.
Fruit/seed production: No fruits/seeds detected to date.

What is claimed is:

1. A new and distinct cultivar of *Phalaenopsis* plant named 'SUPHAL1306' as herein illustrated and described.

* * * * *